US008988767B2

(12) United States Patent
Foltynowicz et al.

(10) Patent No.: US 8,988,767 B2
(45) Date of Patent: Mar. 24, 2015

(54) METHOD AND SYSTEM FOR NON-MECHANICAL RAPID TUNING OF AN OPTICAL PARAMETRIC OSCILLATOR

(75) Inventors: Robert Foltynowicz, Smithfield, UT (US); Michael Wojcik, Mendon, UT (US)

(73) Assignee: Utah State University Research Foundation, North Logan, UT (US)

( * ) Notice: Subject to any disclaimer, the term of this patent is extended or adjusted under 35 U.S.C. 154(b) by 315 days.

(21) Appl. No.: 13/160,737

(22) Filed: Jun. 15, 2011

(65) Prior Publication Data

US 2012/0002689 A1 Jan. 5, 2012

Related U.S. Application Data

(60) Provisional application No. 61/360,293, filed on Jun. 30, 2010.

(51) Int. Cl.
| | |
|---|---|
| *G02F 1/39* | (2006.01) |
| *H01S 3/10* | (2006.01) |
| *G01N 21/39* | (2006.01) |
| *G02F 1/35* | (2006.01) |

(52) U.S. Cl.
CPC .......... *G02F 1/39* (2013.01); *G02F 2001/3542* (2013.01); *G02F 2001/392* (2013.01); *G01N 21/39* (2013.01); *H01S 3/10* (2013.01); *G01N 2021/394* (2013.01)
USPC ................................ 359/330; 372/21; 372/28

(58) Field of Classification Search
None
See application file for complete search history.

(56) References Cited

U.S. PATENT DOCUMENTS

| | | | |
|---|---|---|---|
| 5,841,570 A | 11/1998 | Velsko | |
| 6,421,166 B1 | 7/2002 | Velsko et al. | |
| 6,980,354 B1 * | 12/2005 | Smith et al. | 359/330 |
| 7,630,418 B2 * | 12/2009 | Franjic et al. | 372/21 |
| 8,218,588 B1 | 7/2012 | Bartholomew et al. | |
| 2008/0089369 A1 | 4/2008 | Luo et al. | |

FOREIGN PATENT DOCUMENTS

| | | |
|---|---|---|
| JP | 10268369 A | 10/1998 |
| WO | 2004049056 A1 | 6/2004 |
| WO | 2005053119 A1 | 6/2005 |

OTHER PUBLICATIONS

Webb, High-average power KTiOAsO4 optical parametric oscillator. Optics Letters, Feb. 2, 1998, 1161-1163, vol. 23, No. 15.
(Continued)

*Primary Examiner* — Hemang Sanghavi (57) ABSTRACT

An OPO is disclosed capable of rapid frequency tuning by non-mechanical means. The OPO includes a resonant cavity including one or more non-linear crystals in an optical path thereof. A pump laser pulse is transmitted into the resonant cavity simultaneously with a seed beam having a desired wavelength. The output beam from the resonant cavity has the same center wavelength as the seed beam. The wavelength of the seed beam may be modulated at a frequency larger than the pulse rate of the pump laser or larger than the inverse of the pulse duration. The OPO disclosed may be used to perform DIAL analysis wherein intra-pulse modulation of an output beam is used to obtain measurements of absorption at multiple frequencies for each pulse of a pump beam.

22 Claims, 8 Drawing Sheets

(56) References Cited

OTHER PUBLICATIONS

Gong, Eye-safe compact scanning LIDAR technology, Optics and Lasers in Engineering, Apr. 12, 2007, 898-906, vol. 45, Cambridge MA.

Isyanova Y and Moulton P, Injection-seeded, pump-enhanced, tunable KTA OPO, Conference paper, Optical Society of America, Advanced Solid State Lasers, Feb. 15, 2000,1-10, Q-Peak Inc., Bedford MA.

Chaung, A KTA optical parametric oscillator pumped by a Q-switched, injection seeded Nd:YAG laser, Conference Paper, Optical Society of America, Advanced Solid State Lasers, 1996.

International Search Report and the Written Opinion of the International Searching Authority for PCT/US2012/057317, transmitted Apr. 30, 2013.

Feb. 25, 2014 Non-final Office Action for Continuation-in-Part U.S. Appl. No. 13/627,421.

* cited by examiner

METHOD AND SYSTEM FOR NON-MECHANICAL RAPID TUNING OF AN OPTICAL PARAMETRIC OSCILLATOR

RELATED APPLICATIONS

This patent claims the benefit of U.S. Provisional Application 61/360,293, filed Jun. 30, 2010 and entitled METHOD AND SYSTEM FOR NON-MECHANICAL RAPID TUNING OF AN OPTICAL PARAMETRIC OSCILLATOR, which is hereby incorporated herein by reference.

BACKGROUND

1. The Field of the Invention

This invention relates to apparatus, methods, and systems for tuning optical beams, and in particular, to methods and systems for generating comparatively high pulse energies with an ability to change wavelengths.

2. The Background Art

Eye-safe lasers, having wavelengths in the 1.4 to 2.1 µm range, are used in a wide variety of systems for remote sensing and other applications. Remote sensing instruments use LIDAR (Light Detection and Ranging) techniques for chemical determination, aerosol characterization, and range measurements. For these remote sensing techniques, in which humans may find themselves in the path of the laser, it is important for the laser pulses to be in the eye-safe regime.

The utility of eye-safe lasers is not limited to remote sensing applications. Eye-safe lasers are used in telecommunication equipment and medical systems and find applications in velocimetry techniques and materials processing.

Optical parametric oscillators (OPO) are a type of system that can be used to generate eye-safe laser pulses. An optical parametric oscillator is a light source similar to a laser, but based on optical gain from parametric amplification in a nonlinear crystal rather than stimulated emission. Parametric amplification is a phenomenon where a signal wave can be amplified using a $\chi^2$ or $\chi^3$ optical nonlinearity in a crystal medium together with a pump wave. For an OPO system, a $\chi^2$ nonlinearity in the crystal is required to produce frequency conversions.

Optical parametric oscillators (OPO) are utilized in spectroscopy and other scientific applications where it is desired to cover very broad spectral regions and to deliver outputs with narrow linewidths and high power. Typical OPO frequency tuning requires the mechanical movement of the crystal. Changing the angle of the crystal relative to the pump beam results in a different optical path through the crystal. Thus, different wavelength signal and idler beams are produced.

This method for OPO frequency tuning may rely on changing the angle of the crystal or the angle of incidence of the pump beam. The latter can be accomplished by physically moving the pump laser or adjusting the optical components to redirect the pump beam. Mechanical OPO tuning has associated problems encountered with position accuracy, repeatability, and optical alignment inherent in systems with moving parts. Other tuning techniques include changing the temperature or pressure of the crystal or applying a large voltage to the crystal.

BRIEF SUMMARY OF THE INVENTION

The invention has been developed in response to the present state of the art and, in particular, in response to the problems and needs in the art that have not yet been fully solved by currently available apparatus and methods. The invention provides for more accurate and rapid tuning of an OPO without mechanical means or any other modification of the properties of a non-linear crystal included in the OPO. The features and advantages of the invention will become more fully apparent from the following description and appended claims, or may be learned by practice of the invention as set forth hereinafter.

In one aspect of the invention, a method for operating a laser includes generating pump pulses at a pump wavelength and at a pulse frequency. The pump pulses are transmitted into a resonant cavity having a non-linear crystal in an optical path thereof. The non-linear crystal is operable to emit light in a band of lasing wavelengths that includes wavelengths different from the pump wavelength. A seed beam is generated having a selected wavelength lying within the band of lasing wavelengths. The seed beam is transmitted into the resonant cavity. The selected wavelength of the seed beam is further modulated at a frequency greater than or equal to the pulse frequency.

In another aspect of the invention, the pump pulses have a pulse duration. The selected wavelength may be modulated at a frequency greater than or equal to an inverse of the pulse duration.

A corresponding laser system suitable for performing the above-described method is also disclosed and claimed.

In another aspect of the invention, an OPO laser system is used to perform a differential absorption light detection and ranging (DIAL) method. The method includes outputting a first seed beam, having a first frequency, from a seed laser, the first frequency having a first absorption rate for a gas of interest. A first pump pulse is generated by a pump laser. The first seed beam and first pump pulse are simultaneously transmitted into a resonant cavity.

A first output beam having the first frequency is transmitted from the resonant cavity to a region of interest as a result of the first pump pulse and first seed beam. A first measurement is performed of a portion of the first output beam reflected from the region of interest. A second seed beam having a second frequency is then output from the seed laser into the resonant cavity simultaneously with a second pump pulse.

A resulting second output beam is then transmitted from the resonant cavity to the region of interest. A second measurement of a portion of the second output beam reflected from the region of interest is then made. The first and second measurements are then analyzed to characterize the gas of interest within the region of interest.

In another aspect of the invention, a method for performing DIAL analysis includes selecting a frequency range including first and second frequencies, the first and second frequencies having substantially different absorption rates for a gas of interest. A seed beam is generated having a time varying frequency sweeping through the frequency range during a first time interval.

A pump pulse is generated having a pulse duration at least as long as the first time interval. The seed beam and pump pulse are simultaneously transmitted into a resonant cavity containing a non-linear crystal in an optical path thereof.

As a result, the resonant cavity transmits an output beam toward a spatial region of interest. A portion of the output beam reflected from the region of interest is repeatedly measured. The measurements are then analyzed to characterize the gas of interest within the region of interest.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 1:
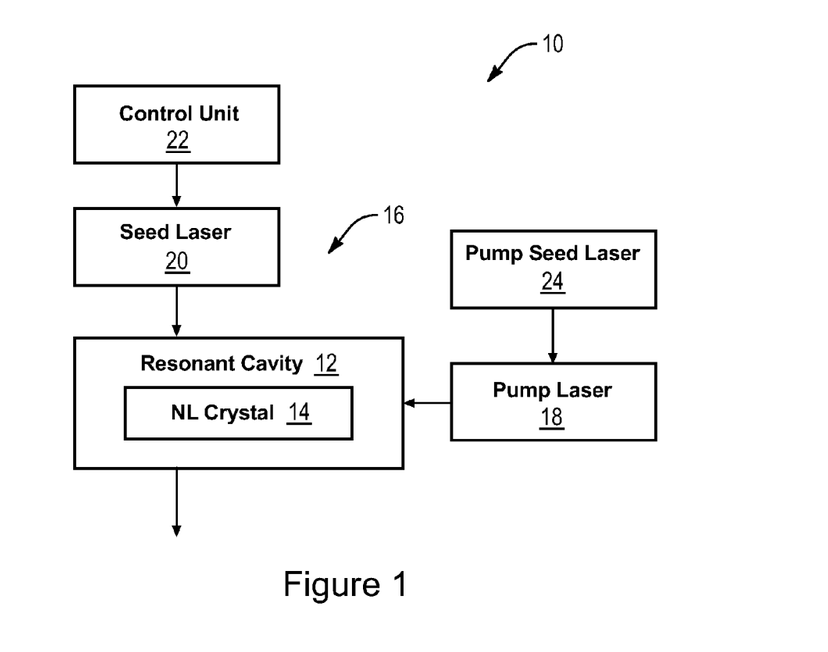
FIG. 1 is a schematic block diagram of an embodiment of an OPO system in accordance with the present invention.

Referring to FIG. 1, an optical parametric oscillator (OPO) system 10 includes a resonant cavity 12 having a non-linear crystal 14 located in an optical path of the resonant cavity 12. The combination of non-linear crystal 14 and resonant cavity 12 may define an OPO 16.

A pump laser 18 transmits pulses into the resonant cavity 12. The pulses have a pulse wavelength and corresponding frequency and are emitted periodically at a pulse rate. The pulses likewise have a pulse duration that is less than the inverse of the pulse rate (the pulse period). The OPO 16 may further include a seed laser 20 that transmits a seed beam into the resonant cavity 12.

A control unit 22 embodied as a general purpose computer or application specific circuit may generate signals for powering one or both of the pump laser 18 and seed laser 20. In some embodiments, a pump seed laser 24 emits a pump seed beam into the pump laser 18 and may also be controlled by the control unit 22.

Figure 2:
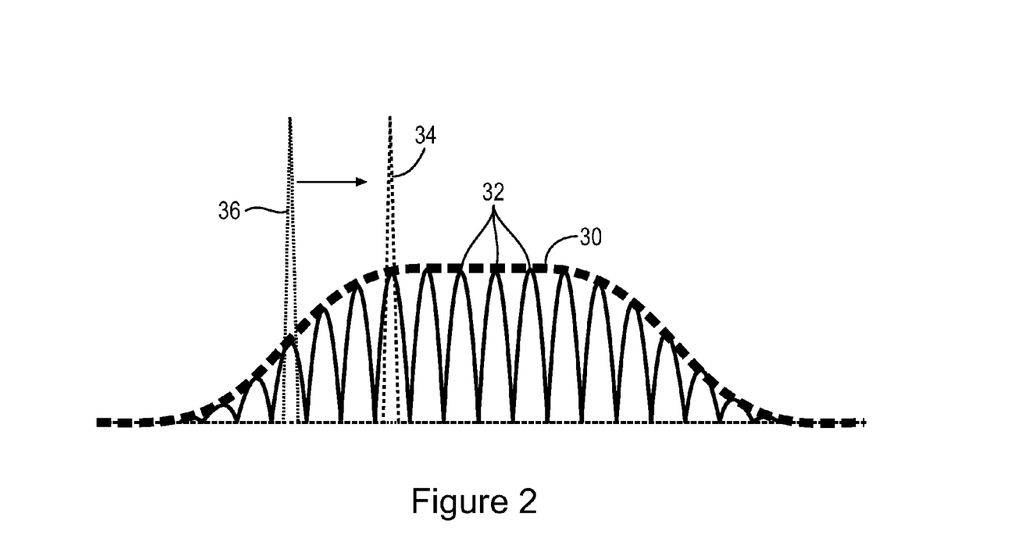
FIG. 2 is a plot of the gain bandwidth and resonant modes of an OPO.

Referring to FIG. 2, the resonant cavity 12 and non-linear crystal 14 define both a gain bandwidth 30 and a plurality of cavity modes 32 that are bounded by the gain bandwidth 30. The gain bandwidth 30 results from properties of the non-linear crystal and the wavelength of the pump laser. It is the range of frequencies or corresponding wavelengths at which light amplification will occur within the non-linear crystal when powered by the pump laser 18.

The cavity modes 32 represent the frequencies or wavelengths at which standing waves can occur within the resonant cavity 12 and will therefore be significantly amplified. Each of the modes 32 lying within the gain bandwidth 30 will be amplified and be present in the output beam of the resonant cavity 12 when only the pump laser is transmitted into the resonant cavity 12.

The seed laser 20 transmits light into the resonant cavity 12 at a frequency or wavelength within the gain bandwidth 30 and results in selection of one of the modes 32 corresponding to the frequency of the seed laser 20. Photons of the seed laser beam incident on the non-linear crystal 14 result in additional photons with identical phase, wavelength, and frequency being emitted from the crystal. Accordingly, the seed laser 20 ensures that photons having the seed laser frequency will dominate and reduce the number of photons corresponding to the other modes 32.

The seed laser 20 is frequency tunable and therefore can be modulated to select one of the modes 32 and thereby control the output of the resonant cavity 12 within the bounds of the gain bandwidth 30. For example, a first frequency profile 34 corresponds to a first frequency mode 32 of the frequency modes 32. It can be obtained by transmitting a seed beam, having a center frequency proximate the center frequency of the first frequency profile 34, into the resonant cavity 12.

By modulating the seed laser 20 to a second frequency, a second frequency profile 36 with a center frequency at a different mode 32 is obtained at the output of the resonant cavity. Note that no modification of the resonant cavity 12 or properties of the non-linear crystal 14 is required. Frequency modulation of the output of the OPO 16 is therefore limited only by the modulation frequency of the seed laser and the relaxation oscillation response of the OPO 16.

Figure 3:
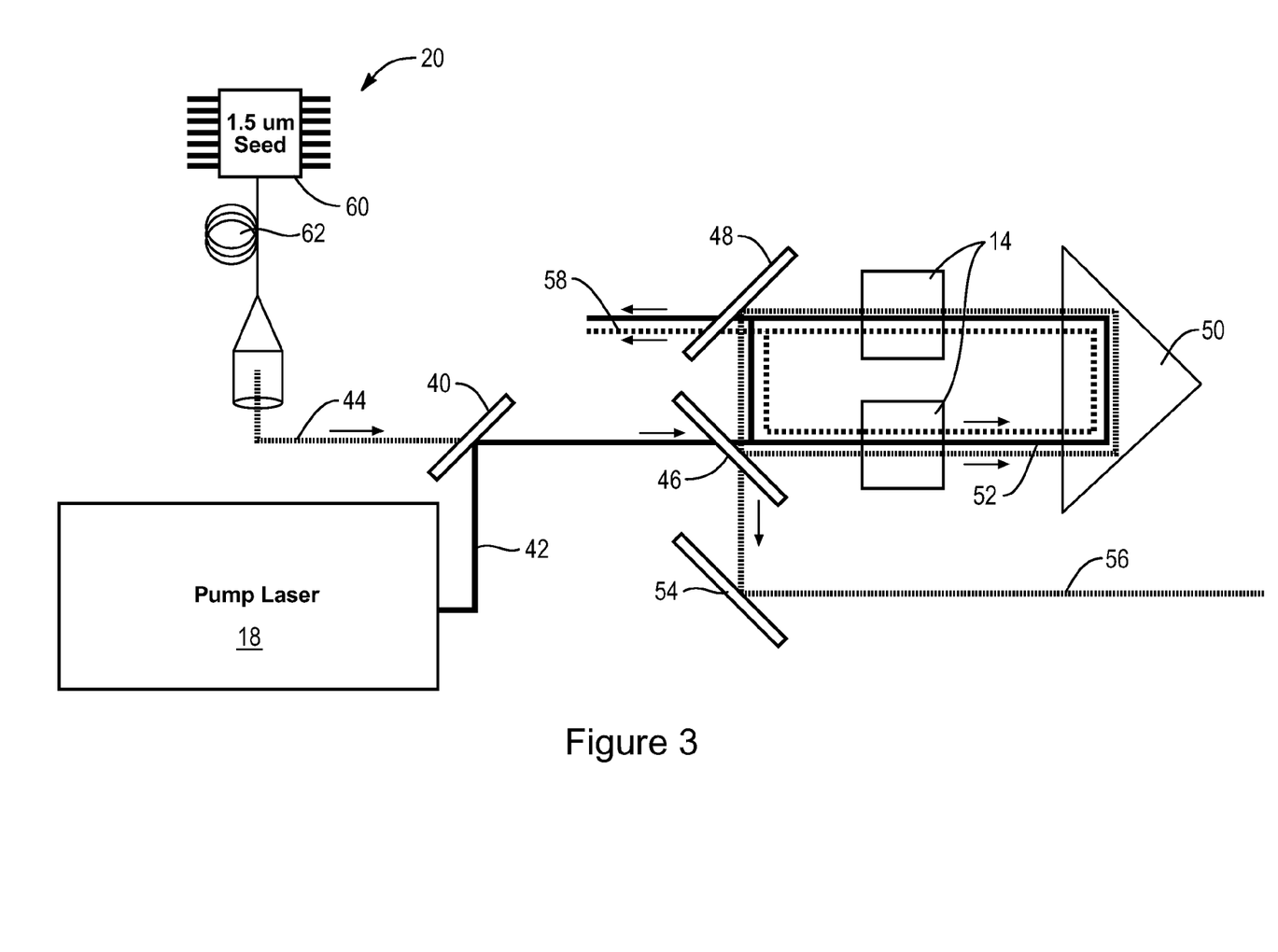
FIG. 3 is a schematic block diagram of an implementation of one embodiment of an OPO system in accordance with the present invention.

FIG. 3, illustrates an implementation of an OPO system 10. In the illustrated embodiment, the pump laser 18 may be, for example, a laser of type Nd:YAG, Nd:YLF, Tm:YAG, Ho:YAG, Er:YAG, or the like. In particular, a high power, single mode, Q-switched Nd:YAG, laser injection seeded at 1064 nm, has been found to be workable.

The pump laser 18 typically emits at a wavelength different from that of the output beam of the OPO system 10. For example, in the illustrated implementation where an Nd:YAG pump laser 18 is used, the pump wavelength may be 1064 nm and the output wavelength may be 1.5 μm.

A typical non-linear crystal emits at two wavelengths when excited by a pump laser. The two wavelengths are called the idler beam and signal beam by convention. In the illustrated embodiment, the signal beam is the output and the idler beam has a wavelength of 3.4 μm.

A dichroic mirror 40 combines a pump beam 42 emitted by the pump laser 18 and a seed beam 44 emitted from the seed laser 20. As in FIG. 3, the pump beam 42 and seed beam 44 are incident on opposing surfaces of the dichroic mirror 40, which is oriented at an angle of 45 degrees with respect to each beam 42, 44. The dichroic mirror 40 may be highly reflective at the pump laser wavelength and transmissive at the seed laser wavelength.

The resonant cavity 12 may be a ring resonator cavity defined by two dichroic mirrors 46, 48 and a turning prism 50 that establish a rectangular path followed by a circulating beam 52 within the resonant cavity 12. Other resonant cavity configurations known in the art may also be used, including, but not limited to, a linear optical path OPO cavity.

The circulating beam 52 may propagate in the counter clockwise direction such that light transmitted through the mirror 46 is incident on the turning prism 50, which redirects incident light onto the mirror 48. The mirror 48 directs incident light onto the mirror 46, and the cycle continues.

The illustrated resonant cavity 12, using a turning prism and dichroic mirrors 40, 46, and 48, enables isolation of the pump laser 18 from the resonant cavity without the use of a Faraday isolator. However, other resonant cavities making use of Faraday isolators may also benefit from the present invention.

The dichroic mirror 48 may be highly reflective of the signal beam wavelength, (the desired output). A diagnostic beam 58 including light having the pump and idler wavelengths may therefore be transmitted through the dichroic mirror 48. The diagnostic beam 58 may be measured for monitoring purposes.

The dichroic mirror 46 may be partially transmissive at the signal wavelength such that a portion of the circulating beam 52 at the signal wavelength will remain within the resonant cavity 12 and a portion will be emitted through the mirror 46. Light transmitted through the dichroic mirror 46 may be incident on another dichroic mirror 54 that is tuned to be highly reflective at the signal wavelength. The output beam 56 reflected from the dichroic mirror 54 will therefore include almost exclusively light at the signal wavelength.

The non-linear crystals 14 may be located across the circulating beam 52. In the illustrated embodiment, two non-linear crystals 14 are located between the mirror 46 and the turning prism 50 and between the mirror 48 and the turning prism 50, respectively. In some embodiments, four non-linear crystals 14 are used. For example, each non-linear crystal 14 in FIG. 3 may be replaced by two non-linear crystals 14.

The non-linear crystals 14 may include potassium titanyl arsenate (KTA) crystals. The non-linear crystals 14 may also include other nonlinear media known in the art, including, but not limited to, potassium titanyl phosphate (KTP), rubidium titanyl arsenate (RTA), lithium niobate (LiNbO3), silver gallium sulphide ($AgGaS_2$), silver gallium selenide ($AgGaSe_2$), zinc germanium diphosphide ($ZnGeP_2$), cadmium selenide (CdSe), potassium dihydrogen phosphate (KDP), barium boron oxide (BBO), lithium boron oxide (LBO), and cesium lithium borate (CLBO).

The non-linear crystals 14 may be, but not limited to, non-critical phase matching (NCPM) crystals that allow a large acceptance angle for the pump laser 18, such as the illustrated pump laser 18 embodied as a single mode pump source. In addition, given the large bandwidth acceptance at NCPM, the seed laser 20 can drive the OPO system 10 to emit at arbitrary injection seeded wavelengths of frequencies across a wide wavelength or frequency band. An alternative to NCPM would be, for example, critically phase matched geometries, though, with reduced tuning ranges.

Note that no mechanical tuning is required to obtain a change in wavelength at the output of the OPO system 10. The resonant cavity 12 may be actively stabilized using a piezo transducer or other line-locking (e.g., dithering) schemes to further enhance the frequency control of the resonant cavity 12.

However, the position or orientation of the non-linear crystals 14 in the system is preferably fixed. The angle of the non-linear crystals is also preferably not changed to tune the output signal. Likewise, the angle of incidence of the pump beam 42 and seed beam 44 with respect to the non-linear crystals 14 is also preferably fixed.

In some embodiments, the gain bandwidth 30 may be shifted by altering one or more of the orientation, temperature, and pressure of the non-linear crystals 14 or by altering an applied voltage. Modification of the angle of incidence of a pump beam may also be used. Shifting may enable access to a different frequency band within which rapid tuning may occur. However, rapid frequency tuning above the pulse rate or at a modulation frequency above the inverse of the pulse duration is preferably performed by frequency modulation of the seed laser 20.

The seed laser 20 may be embodied as a laser diode 60 coupled to the resonant cavity 12 by means of a fiber optic cable 62. However, any laser known in the art that can be rapidly tuned by current or voltage at frequencies comparable to the pulse rate or the inverse of the pulse duration may be used.

A frequency agile 1.5 μm diode laser that produces a narrow linewidth signal wave at 1.533 μm has been found to provide good performance. Laser diodes are frequency tunable by modulating a drive current and therefore provide a high degree of frequency agility. For example, a laser diode may have a wavelength modulation frequency as large as 100 GHz, or even higher.

The laser diode 60 may have a wavelength modulation frequency greater than or equal to the pulse rate or the inverse of the pulse duration. For example, in the illustrated embodiment, the pump laser 18 may have a pulse rate of 30 Hz with a pulse duration of 10 ns. The laser diode 60 in such an embodiment preferably has a wavelength modulation frequency that is preferably greater than or equal to about 30 Hz, more preferably greater than or equal to about 100 MHz (1/(10 ns)).

Experiments conducted by the inventors have obtained conversion rates of 50% for the configuration of FIG. 3 as described hereinabove. In contrast, conventional OPO systems have a conversion frequency of between 35% and 50%. The pump laser tested had a wavelength of 1064 nm and had a bandwidth of 90 MHz.

Upon interaction with the KTA non-linear crystals 14 used, a 1.5 μm signal beam was generated with bandwidth of approximately 60 GHz. To narrow the bandwidth of the 1.5 μm signal beam, a 1.5 μm seed laser 20 was used to select a mode from this 60 GHz bandwidth. As a result, the bandwidth of the 1.5 μm OPO output went from 60 GHz to about 120 MHz. As described above with respect to FIG. 2, any mode within the 60 GHz bandwidth may be selected by tuning to it of the wavelength of the seed laser 20.

Figure 4:
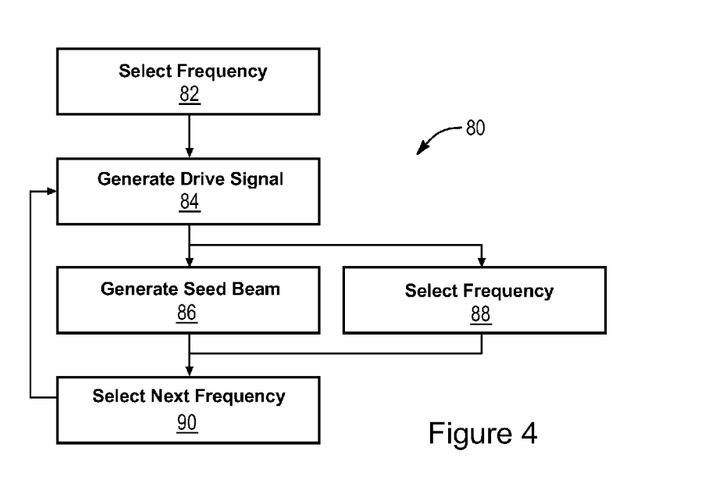
FIG. 4 is a process flow diagram of an embodiment of a method for operating an OPO system in accordance with the present invention.

FIG. 4 illustrates a method 80 for operating an OPO system, such as the OPO system 10 described hereinabove. The method 80 may be executed by an operator, by a control unit 22, or by a combination thereof. A frequency is selected 82, and a drive signal having a current and/or voltage effective to obtain the selected frequency is then generated 84. For purposes of this disclosure frequency and wavelength may be used interchangeably, due to their relation used to describe light. Accordingly, selecting 82 a frequency may include selecting 82 a wavelength.

The seed laser 20 is driven with the control signal to generate 86 a seed beam having the selected frequency or wavelength. A pump pulse is also generated 88. The seed beam and pump pulse may be generated simultaneously or may substantially overlap in time (e.g., greater than 80%, preferably greater than 90%, of the pulse duration). As shown in FIG. 3, the seed beam and pump pulse are transmitted into the resonant cavity. As described hereinabove, the result is an output signal that has a center frequency and wavelength equal to the seed beam frequency and wavelength.

A second frequency or wavelength is then selected 90, and a corresponding drive signal is generated 84. The seed laser 20 is again driven with the drive signal to generate 86 a seed beam, and a pump pulse is again generated 88, substantially overlapping the seed beam in time. The selection step 90 and generation steps 84-88 are preferably performed such that the seed laser 20 is emitting at the selected next frequency or wavelength by the time the next pulse is generated 88. That is, immediately following the pulse generated 88 in the previous pulse generation step 88, a new pulse is generated 88 according to the specified pulse rate of the pump laser 18. As noted above, this requires modulating the frequency and wavelength of the seed laser 20 at a frequency greater than the pulse rate.

Figure 5:
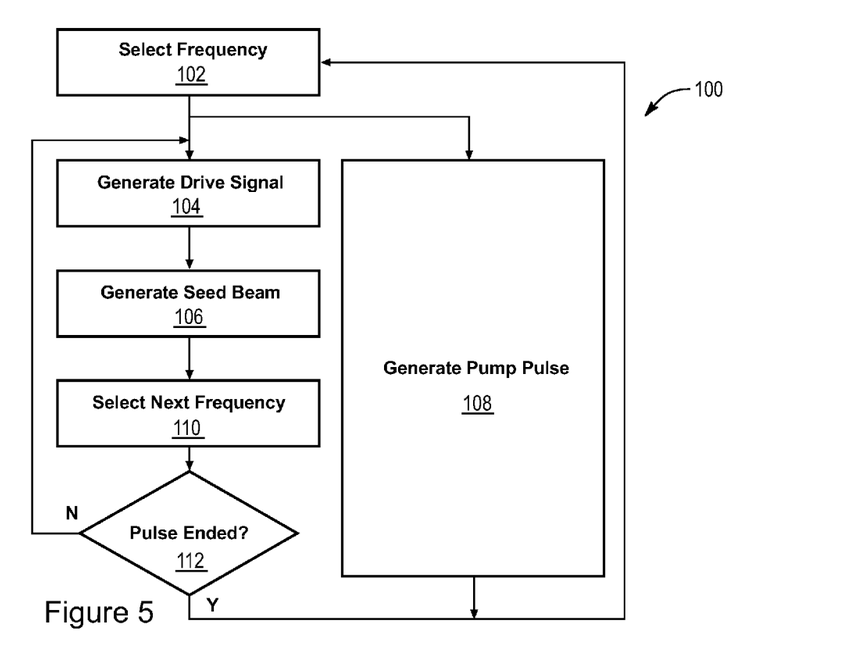
FIG. 5 is a process flow diagram of an alternative method for operating an OPO system.

FIG. 5 illustrates an alternative method 100 for operating an OPO system, such as the OPO system 10 described hereinabove. The method 100 includes selecting 102 a first frequency or wavelength. A drive signal having a controlled voltage, current, or both effective to cause the seed laser 20 to emit at the selected frequency or wavelength is then generated 104. The seed laser 20 is driven with the drive signal to generate 106 a seed beam having the selected frequency or wavelength. A pump pulse is generated 108 so as to substantially overlap in time with the seed beam.

A second frequency is then selected 108. If the pulse is found 112 not to have ended, then, steps 104 and 106 are repeated. Otherwise, the method repeats starting at step 102. Steps 104, 106, and 110 may be performed repeatedly during generation 108 of a single pump pulse. Steps 104, 106, 110 may be performed in a continuous fashion such that the seed beam sweeps continuously across a range of frequencies during generation 108 of a single pump pulse.

As described hereinabove, the pump pulse and seed beam emit into the resonant cavity 12. As also described above, as the frequency of the seed beam is changed, the frequency of the output beam of the GPO system 10 also changes. Evaluating 112 whether a pump pulse may be omitted may be based on prior knowledge of the duration of the pulse. In such a case evaluating 112 whether the pump pulse has ended may be omitted.

Figure 6:
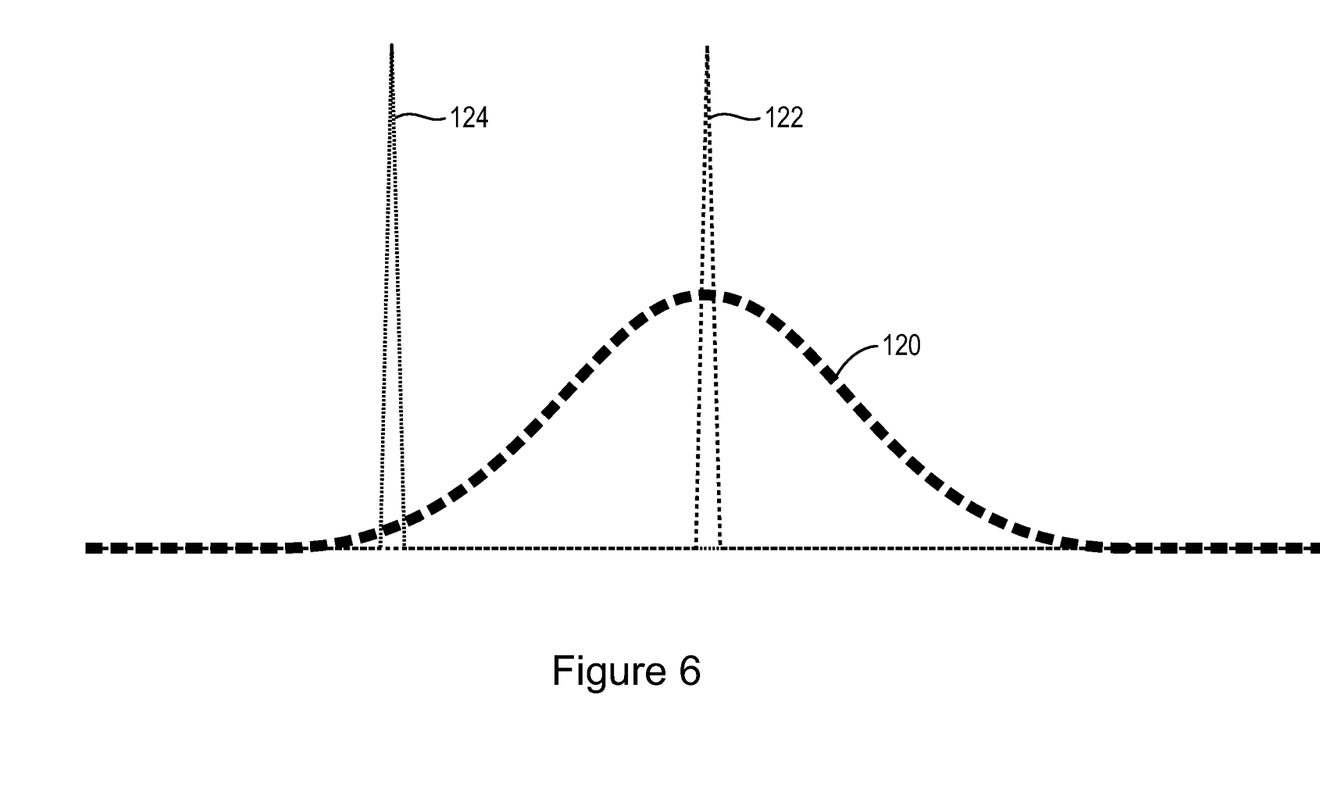
FIG. 6 is a plot of a gas absorption band and OPO output frequencies.

Referring to FIG. 6, the novel OPO system 10 and methods of use 80, 100 may be used to perform differential absorption light detection and ranging (DIAL). Gases within the atmosphere have an absorption spectrum with multiple bands of high absorption. Line 120 represents one absorption band of a gas of interest. In DIAL, gas within a region of interest is irradiated with a beam having a first frequency 122 and the amount of light reflected is measured. Gas within the region of interest is then irradiated with a beam having a second frequency 124. The amount of light reflected from the region of interest is again measured.

One of the frequencies 122, 124 is chosen to lie within the absorption band 120 at a region of high absorption. The other of the frequencies 122, 124 is chosen to be a frequency at which little absorption occurs for the gas of interest. For example, absorption at one of the frequencies 122, 124 may be 10% to 90% less than the absorption at the other of the frequencies 122, 124. In some methods, more than one frequency may be used in the high absorption region and more than one may be used in the low absorption region.

The measurement of reflected light at a frequency with little absorption provides a reference for evaluating the measurement of reflected light at a frequency with high absorption. By evaluating these measurements, the concentration of the gas having the given absorption band 120 may be characterized. The measurement and evaluation of measurements of reflected light may be performed according to any methods for performing DIAL known in the art.

Figure 7:
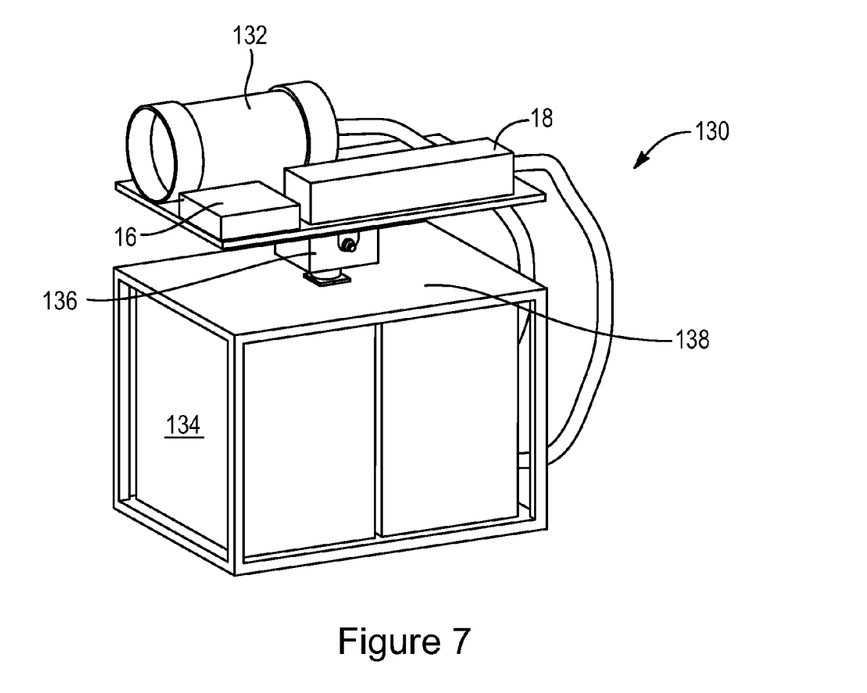
FIG. 7 is an isometric view of an embodiment of a DIAL system in accordance with the present invention.

Referring to FIG. 7 a DIAL system 130 may include a pump laser 18 and an OPO 16 as described hereinabove. The OPO 16 includes the seed laser 20 as described hereinabove in addition to the resonant cavity 12 and non-linear crystals 14. The DIAL system 130 may further include a detector 132 for receiving reflected light from a region of interest and a control unit 134. The detector 132 may include lenses, for focusing received light, and a light sensor. The detector 132, pump laser 18, and OPO 16 may be mounted to orientation actuators 136 for rotating the OPO 16 and detector 132 in both the vertical and horizontal planes. The orientation actuators 136 may mount the pump laser 18, OPO 16, and detector 132 to a housing 138. The control unit 134 may be mounted within the housing 138.

Figure 8:
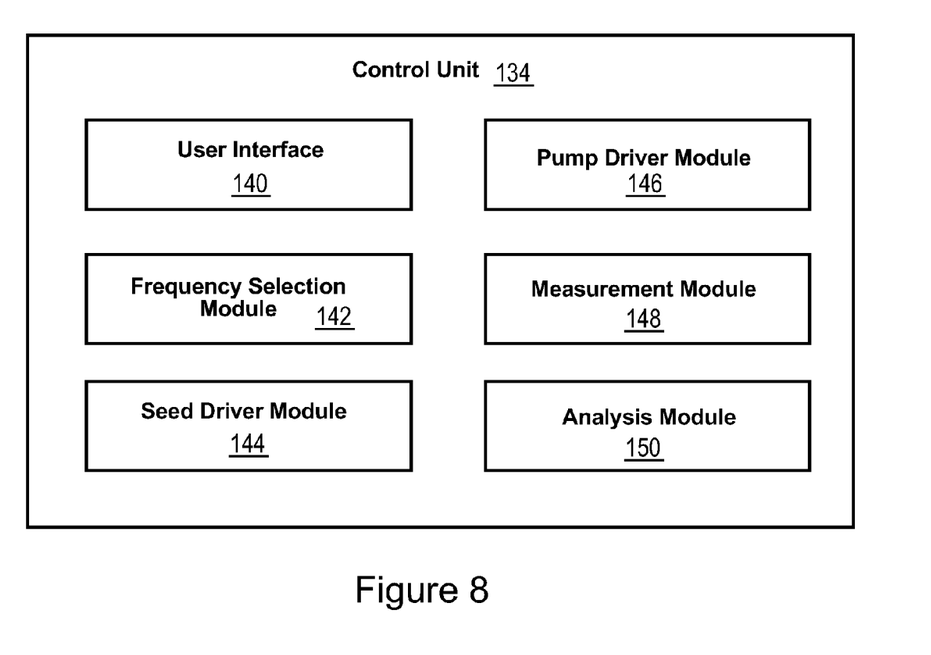
FIG. 8 is a schematic block diagram for an embodiment of a DIAL system in accordance with the present invention.

Referring to FIG. 8, the control unit 134 may be embodied as a general purpose computer or application-specific computing device. The control unit 134 may include a user interface 140 for receiving user instructions and presenting output data. The user interface 140 may include a display screen, keyboard, touch screen, pointing device, or any other data input and output device known in the art.

The control unit 134 may further include a frequency selection module 142 that determines at which frequency or wavelength the OPO 16 will emit. The frequency selection module 142 may be instructed to switch between different frequencies at a switching frequency greater than the pulse rate or greater than the inverse of the pulse duration of the pump laser 18. The frequency selection module 142 may also be instructed to sweep continuously between two frequencies. The frequency selection module 142 may simply receive a frequency value specified by the user using the user interface 140.

The output of the frequency selection module 142 may be input to a seed driver module 144. The module 144 generates an electrical signal having a voltage and current effective to cause the seed laser 20 to emit at the frequency or wavelength identified by the frequency selection module 142. The output of the seed driver module 144 is coupled to the seed laser 20.

The pump driver module 146 generates a drive signal for the pump laser 18. This may include generating a drive signal for the pump seed laser 24. The pump driver module 146 may generate a pulsed or continuous drive signal and may simply generate a drive signal in response to a user instruction turning on the pump laser 18. Where the pump laser 18 has a tunable frequency, amplitude, pulse rate, pulse duration, or combination thereof, the pump driver module 146 may translate instructions, intended to achieve a desired value for these parameters, into the appropriate drive signal.

The control unit 134 may also include a measurement module 148 that receives the output of the detector 132. The measurement module 148 may include any device, software module, or both, known in the art to be capable of measuring back-scattered light in a DIAL system. The control unit 134 may further include an analysis module ISO including any device, software module, or both, known in the art to be capable of analyzing DIAL measurements in order to characterize gas in a region of interest.

Figure 9:
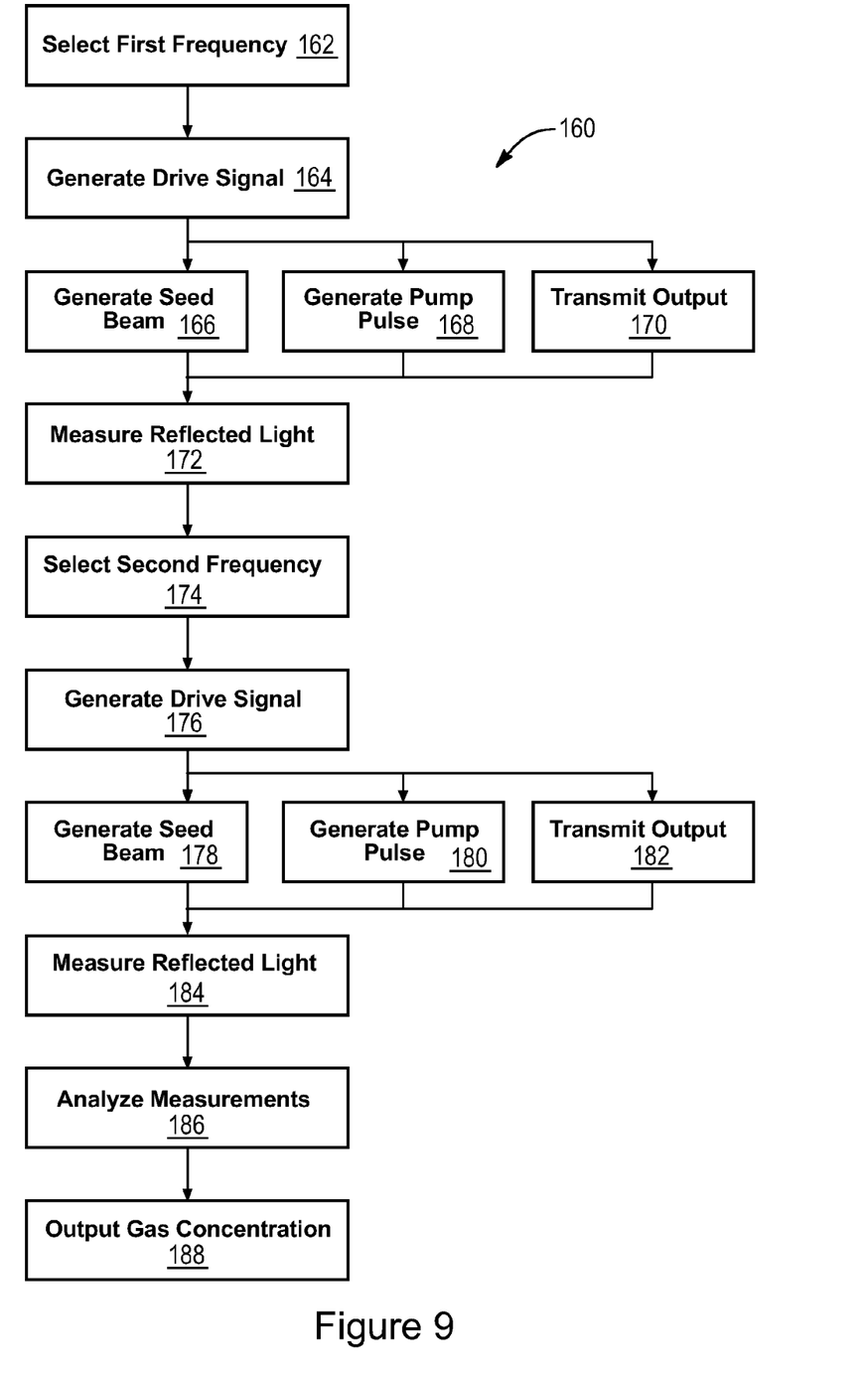
FIG. 9 is a process flow diagram of an embodiment of a method for operating a DIAL system in accordance with the present invention.

Referring to FIG. 9, a DIAL system, such as the DIAL system 130, may be used to perform the illustrated method 160. A first frequency or wavelength is selected 162. The first frequency may be a high absorption frequency for a gas of interest, e.g., a frequency at which the gas of interest has an absorption within about 10% of its peak absorption for the absorption band containing the first frequency. The first frequency may also be a low absorption frequency, for example, a frequency at which the gas of interest has an absorption substantially less, (e.g., less than about 90% of the peak) absorption for the absorption band closest to the first frequency.

A drive signal for the seed laser 20 is then generated 164 effective to cause the seed laser 20 to emit the frequency previously selected 162. The seed laser 20 is driven with the drive signal to generate 166 a seed beam having the first frequency. A pump pulse is also generated 168 such that the pump pulse overlaps substantially in time with the seed beam generated at step 166. The output of the OPO 16 is then transmitted 170 toward a region of interest. Light reflected from the region of interest is then measured 172.

A second frequency or wavelength is selected 174, and a corresponding drive signal is generated 176, followed by generation 178 of a seed beam having the second frequency. The second frequency may have an absorption for the gas of interest that is less than or equal to about 10% that of the first frequency. The order may be reversed and the first frequency may have an absorption for the gas of interest that is less than or equal to about 10% of that of the second frequency. A pump pulse is also again generated 180 such that the second pulse overlaps substantially in time with the seed beam generated at step 176. The output of the OPO 16 is then again transmitted 182 toward the region of interest. Again, light reflected from the region of interest is then measured 184.

The measurements taken at steps 172 and 184 are then analyzed 186 to characterize the concentration of the gas of interest in the region of interest according to methods known in the art of DIAL analysis. Data characterizing the gas of interest within the region of interest may then be output 188 in a human or computer readable form.

Figure 10:
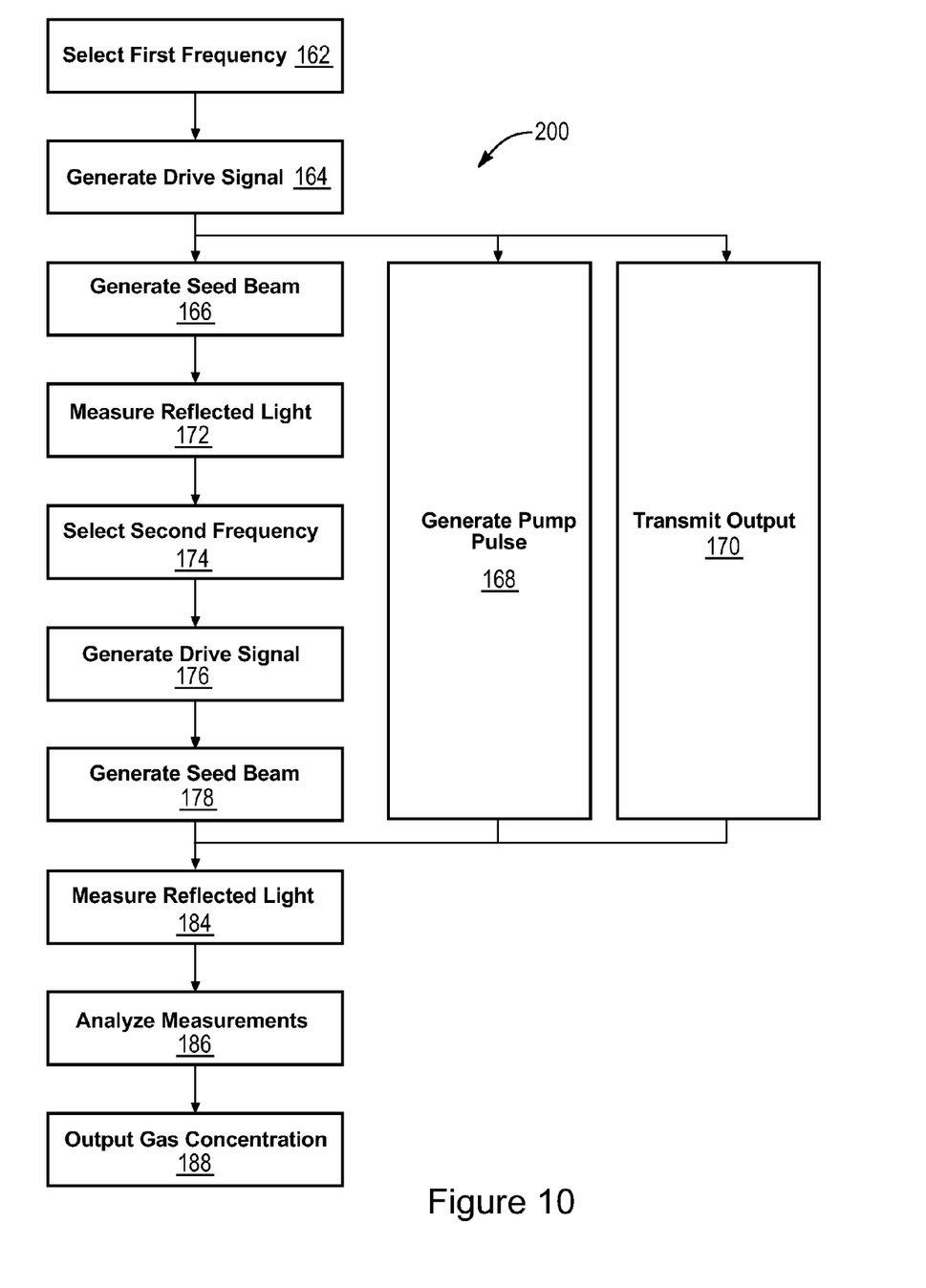
FIG. 10 is a process flow diagram of an embodiment of an alternative method for operating a DIAL system in accordance with the present invention.

Referring to FIG. 10, in an alternative embodiment, a method 200 may be identical to the method 160, with the exception of generating 168 the pump pulse and transmitting 170 the output of the OPO 16. Due to the novel tuning methods disclosed herein, modulation of the output frequency of the OPO 16 may be faster than the pulse rate or the inverse of the pulse duration. Accordingly, generating 168 the pump pulse and transmitting 170 the output of the OPO 16, may substantially overlap in time both generating 166 the seed beam at the first frequency and generating 178 the seed beam at the second frequency, such that the second pulse generation step 180 and second transmitting step 182 may be omitted.

Accordingly, the output of the OPO 16 corresponding to a single pump pule will include portions at the first frequency and at the second frequency. Measuring 172 reflected light and measuring 184 the reflected light may occur at appropriate times to measure the portion of reflected light corresponding to portions of the OPO output corresponding to the first and second frequencies, respectively.

Figure 11:
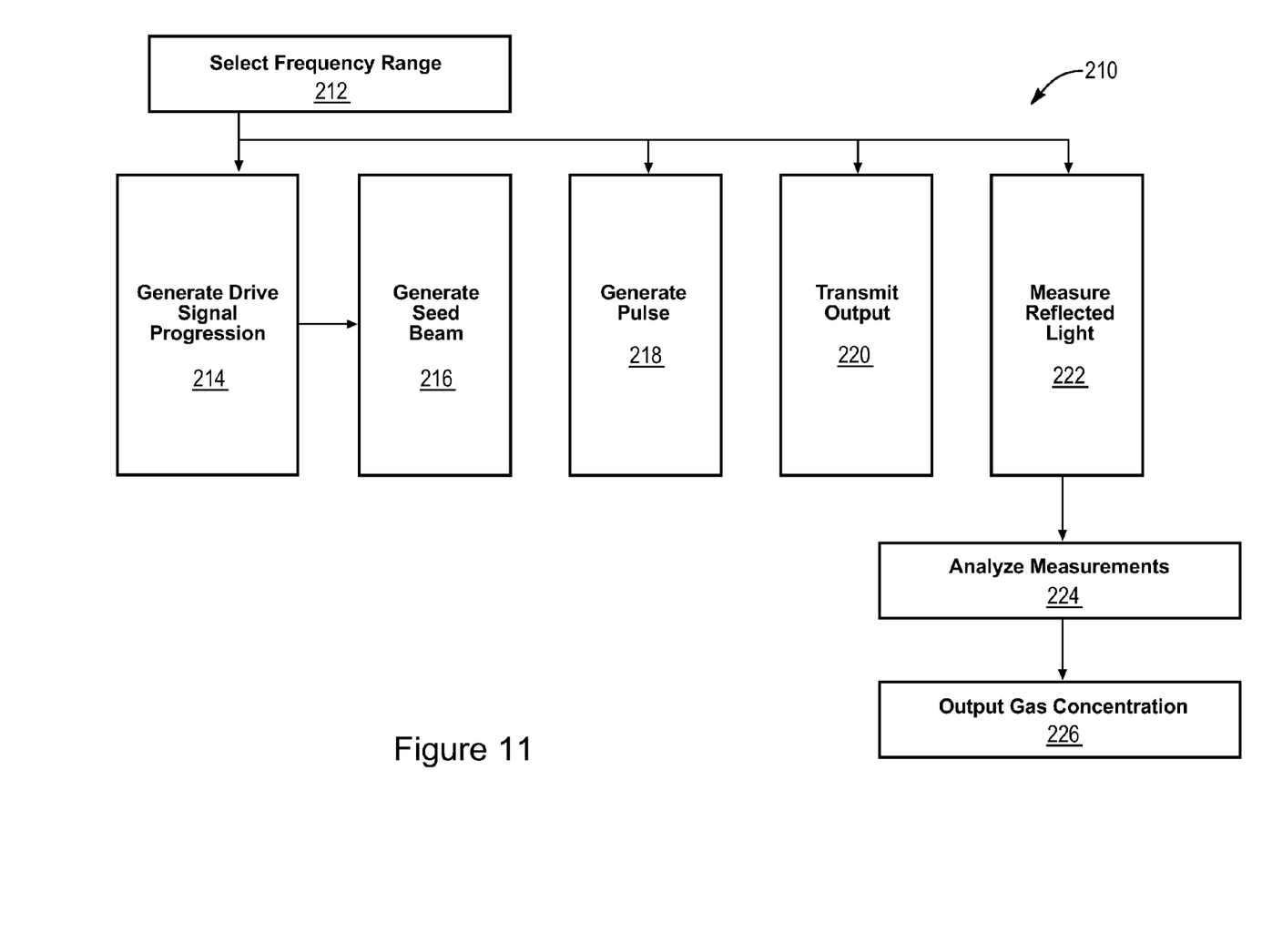
FIG. 11 is a process flow diagram of an embodiment of another alternative method for operating a DIAL system in accordance with the present invention.

FIG. 11 illustrates an alternative method 210 for performing DIAL analysis. In the method 210, a frequency or wavelength range is first selected 212. The frequency range includes frequencies of both high absorption and low absorption for the gas of interest. For example, the frequency range may include first and second frequencies such that absorption at one of the frequencies is less than 10% of that of the other frequency. One of the first and second frequencies may have an absorption that is within 90% of the peak absorption of the absorption band of the gas of interest closest to that frequency.

A drive signal progression is generated 214 that will cause the seed laser 20 to sweep through the frequency range that was selected 212. In response to the drive signal, the seed laser 20 will generate 216 a seed beam that sweeps through the selected frequency range. While the seed beam is being generated 216, a pump pulse is also generated 218 using the pump laser 18. The pump pulse preferably substantially overlaps in time the generation 216 of the seed beam.

As a result of generation 216 of the seed beam and generation 218 of the pump pulse, an output beam is transmitted 220 to a region of interest. Light reflected from the region of interest is repeatedly measured 222. The measurements are then analyzed 224 to determine the absorption at various frequencies within the frequency range that was selected 212. Thus one may characterize the concentration of the gas of interest in the region of interest. Data characterizing the gas of interest within the region of interest may then be output 226 in a human or computer readable form.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for operating a laser system comprising:
    generating with a pump laser pump laser pulses at a pump pulse frequency;
    inputting the pump laser pulses into a resonant cavity positioning a non-linear, non-critical phase matching crystal within the resonant cavity;
    generating multiple cavity modes inside the resonant cavity, each cavity mode being a wavelength at which standing waves occur within the resonant cavity;
    emitting a seed signal from a seed laser into the resonant cavity, the seed signal having a seed wavelength;
    electrically coupling a control unit to the seed laser;
    switching, via the control unit, the seed wavelength between the first seed wavelength and a second seed wavelength, the first seed wavelength having a first center wavelength proximate a first cavity mode and the second seed wavelength having a second center wavelength proximate a second cavity mode, there being at least two cavity modes between the first cavity mode and the second cavity mode; and
    modulating the seed laser at a seed pulse frequency at least as great as the pump pulse frequency.

2. The method of claim 1, wherein the seed laser is a laser diode.

3. The method of claim 1, wherein the crystal is selected from the group consisting of potassium titanyl arsenate (KTA), potassium titanyl phosphate (KTP), rubidium titanyl arsenate (RTA), silver gallium sulphide ($AgGaS_2$), silver gallium selenide ($AgGaSe_2$), zinc germanium di-sulphide ($ZnGeP_2$), cadmium selenide, potassium dihydrogen phosphate (KDP), barium boron oxide (BBO), lithium boron oxide (LBO), caesium lithium boron oxide (CLBO), Lithium Niobate (LiNbO3).

4. The method of claim 3, wherein the crystals are crystals with phase matched geometries.

5. The method of claim 1, wherein the resonant cavity is a ring resonator.

6. The method of claim 1, wherein the width of the band of the multiple cavity modes corresponds to a frequency band of about 60 GHz.

7. The method of claim 1, further comprising positioning a non-linear, non-critical phase matching crystal within the resonant cavity and the non-linear crystal is fixed relative to the resonant cavity.

8. A method for operating a laser comprising:
generating pump pulses at a pump wavelength and at a pump pulse frequency;
transmitting the pump pulses into a resonant cavity having a non-linear, non-critical phase matching crystal in an optical path thereof, the non-linear crystal operable to emit light in a band of lasing wavelengths that includes wavelengths different from the pump wavelength;
generating multiple cavity modes inside a resonant cavity, each cavity mode being a wavelength at which standing waves occur within the resonant cavity;
generating a seed beam having a seed wavelength lying within the band of lasing wavelengths;
transmitting the seed beam into the resonant cavity;
switching the seed wavelength between a first seed wavelength and a second seed wavelength, the first seed wavelength having a first center wavelength proximate a first cavity mode and the second seed wavelength having a second center wavelength proximate a second cavity mode, there being at least two cavity modes between the first cavity mode and the second cavity mode; and
modulating the seed wavelength at a seed modulation frequency greater than or equal to the pump pulse frequency.

9. The method of claim 8, wherein the band of lasing wavelengths has a width corresponding to a frequency band of greater than or equal to about 50 GHz.

10. The method of claim 9, further comprising emitting an output beam from the resonant cavity having an output wavelength band containing the seed wavelength and having a width corresponding to a frequency band of less than or equal to about 200 MHz.

11. The method of claim 8, wherein the band of lasing wavelengths has a width corresponding to a frequency band of greater than or equal to about 60 GHz.

12. The method of claim 11, wherein switching the seed wavelength comprises switching the seed wavelength across a band of frequencies larger than about 200 MHz and less than about 60 GHz.

13. The method of claim 11, further comprising emitting an output beam from the resonant cavity having an output wavelength band containing the seed wavelength and having a width corresponding to a frequency band of less than or equal to about 120 MHz.

14. The method of claim 8, wherein:
generating the seed beam comprises activating a laser diode; and
switching the seed wavelength comprises switching current supplied to the laser diode.

15. The method of claim 8, wherein:
generating pump pulses further comprises generating pulses having a pulse duration; and
modulating the seed wavelength at the seed modulation frequency greater than the pump pulse frequency comprises modulating the seed wavelength at a frequency greater than or equal to an inverse of the pulse duration.

16. The method of claim 8, wherein the crystal is selected from the group consisting of potassium titanyl arsenate (KTA), potassium titanyl phosphate (KTP), rubidium titanyl arsenate (RTA), silver gallium sulphide ($AgGaS_2$), silver gallium selenide ($AgGaSe_2$), zinc germanium di-sulphide ($ZnGeP_2$), cadmium selenide, potassium dihydrogen phosphate (KDP), barium boron oxide (BBO), lithium boron oxide (LBO), cesium lithium boron oxide (CLBO), Lithium Niobate (LiNbO3).

17. The method of claim 8, further comprising actively stabilizing the resonant cavity.

18. The method of claim 8, further comprising maintaining the crystal in a fixed orientation relative to the resonant cavity.

19. A method for operating a laser comprising:
generating pump pulses at a pump frequency and at a pump pulse rate;
transmitting the pump pulses into a resonant cavity having a non-linear crystal in an optical path thereof, the non-linear crystal and resonant cavity operable to emit light in a band of lasing frequencies that includes frequencies different from the pump frequency;
generating a seed beam having a seed frequency, the seed frequency lying within the band of lasing frequencies;
transmitting the seed beam into the resonant cavity;
switching the seed frequency between a first seed frequency and a second seed frequency, the first seed frequency having a first center frequency proximate a first cavity mode and the second seed frequency having a second center frequency proximate a second cavity mode, there being at least two cavity modes between the first cavity mode and the second cavity mode;
emitting an output beam from the resonant cavity, the output beam including the seed frequency and having a bandwidth less than 0.5 percent of that of the band of lasing frequencies; and
modulating the seed frequency at a modulation rate greater than or equal to the pump pulse rate.

20. A method for performing differential absorption light detection and ranging, the method comprising:
outputting a first seed beam having a first frequency from a seed laser, the first frequency having a first absorption rate for a gas of interest;
generating a first pump pulse from a pump laser;
simultaneously transmitting the first seed beam and first pump pulse into a resonant cavity having a non-linear crystal in an optical path thereof;
generating multiple cavity modes inside the resonant cavity, each cavity mode being a wavelength at which standing waves occur within the resonant cavity, the first frequency having a first center frequency proximate a first cavity mode;
transmitting a first output beam from the resonant cavity to a region of interest, the first output beam including light having the first frequency;
making a first measurement of a portion of the first output beam reflected from the region of interest;
outputting a second seed beam having a second frequency from the seed laser, the second frequency having a second absorption rate for the gas of interest and having a second center frequency proximate a second cavity mode, there being at least two cavity modes between the first cavity mode and the second cavity mode;
generating a second pump pulse;
simultaneously transmitting the second seed beam and second pump pulse into the resonant cavity;
transmitting a second output beam from the resonant cavity to the region of interest, the second output beam including light having the second frequency;
making a second measurement of a portion of the second output beam reflected from the region of interest;
analyzing the first and second measurements to characterize the gas of interest within the region of interest.

21. The method of claim 20, wherein the position and orientation of the non-linear crystal with respect to the resonant cavity is the same while simultaneously transmitting the first seed beam and first pump pulse into the resonant cavity and while simultaneously transmitting the second seed beam and second pump pulse into the resonant cavity.

22. The method of claim 21, wherein at least one of:

absorption of the gas of interest at the first frequency is less than ten percent of absorption of the gas of interest at the second frequency; and absorption of the gas of interest at the second frequency is less than ten percent of absorption of the gas of interest at the first frequency.

* * * * *